(12) United States Patent
Nesher et al.

(10) Patent No.: US 11,344,296 B2
(45) Date of Patent: May 31, 2022

(54) DEVICE AND METHOD FOR SUTURING

(71) Applicant: EPIC M.D LTD, Katzerin (IL)

(72) Inventors: Eviatar Nesher, Ein Vered (IL); Shmuel Segal, Ramat Hasharon (IL)

(73) Assignee: EPIC M.D LTD, Katzerin (IL)

( * ) Notice: Subject to any disclaimer, the term of this patent is extended or adjusted under 35 U.S.C. 154(b) by 0 days.

(21) Appl. No.: 15/742,691

(22) PCT Filed: Jul. 6, 2016

(86) PCT No.: PCT/IL2016/050722
§ 371 (c)(1),
(2) Date: Jan. 8, 2018

(87) PCT Pub. No.: WO2017/006321
PCT Pub. Date: Jan. 12, 2017

(65) Prior Publication Data
US 2018/0199937 A1     Jul. 19, 2018

Related U.S. Application Data

(60) Provisional application No. 62/189,277, filed on Jul. 7, 2015.

(51) Int. Cl.
*A61B 17/06*     (2006.01)
*A61B 17/04*     (2006.01)
*A61B 17/064*     (2006.01)

(52) U.S. Cl.
CPC .... *A61B 17/06114* (2013.01); *A61B 17/0401* (2013.01); *A61B 17/0466* (2013.01); *A61B 17/064* (2013.01); *A61B 17/0491* (2013.01); *A61B 17/06123* (2013.01); *A61B 2017/045* (2013.01); *A61B 2017/0409* (2013.01);
(Continued)

(58) Field of Classification Search
CPC ............ A61B 17/06114; A61B 17/064; A61B 17/0466; A61B 17/0401; A61B 2017/0647; A61B 2017/06157; A61B 2017/06142; A61B 17/0491; A61B 2017/0409; A61B 2017/06176; A61B 2017/0464; A61B 2017/0462; A61B 2017/045; A61B 2017/0437; A61B 2017/0417; A61B 2017/0414; A61B 17/06123; A61B 2017/0496; A61B 2017/0474; A61B 2017/0454; A61B 2017/0425; A61B 2017/0408
See application file for complete search history.

(56) References Cited

U.S. PATENT DOCUMENTS 2,944,739 A    7/1960   Schwinn
4,705,040 A * 11/1987   Mueller ........... A61B 17/00234
                                                     604/513
(Continued)

FOREIGN PATENT DOCUMENTS

CN       104684490 A    6/2015
EP       2 361 566 A2    8/2011
(Continued)

*Primary Examiner* — Julian W Woo
(74) *Attorney, Agent, or Firm* — Vorys, Sater, Seymour and Pease LLP; Anthony Venturino

(57) ABSTRACT

Provided is a system, a device, a cassette for use therein and method for suturing two tissue sections, for example two sections of a tissue, by using a plurality of consecutively-arranged anchoring units.

24 Claims, 12 Drawing Sheets

(52) U.S. Cl.
CPC .............. *A61B 2017/0414* (2013.01); *A61B 2017/0417* (2013.01); *A61B 2017/0437* (2013.01); *A61B 2017/0462* (2013.01); *A61B 2017/0464* (2013.01); *A61B 2017/0647* (2013.01); *A61B 2017/06142* (2013.01); *A61B 2017/06157* (2013.01); *A61B 2017/06176* (2013.01)

(56) References Cited

U.S. PATENT DOCUMENTS

| | | | |
|---|---|---|---|
| 5,441,502 A | 8/1995 | Bartlett | |
| 5,810,848 A * | 9/1998 | Hayhurst | A61B 17/04 606/139 |
| 6,500,184 B1 | 12/2002 | Chan et al. | |
| 6,673,094 B1 | 1/2004 | McDevitt et al. | |
| 7,021,316 B2 * | 4/2006 | Leiboff | A61B 17/0401 128/898 |
| 7,713,285 B1 | 5/2010 | Stone et al. | |
| 7,815,655 B2 * | 10/2010 | Catanese, III | A61B 17/0401 606/151 |
| 8,343,187 B2 * | 1/2013 | Lamson | A61B 17/0487 606/232 |
| 9,393,007 B2 * | 7/2016 | Darois | A61B 17/0057 |
| 10,722,224 B2 * | 7/2020 | Stopek | C07D 471/04 |
| 2001/0041916 A1 | 11/2001 | Bonutti | |
| 2003/0105489 A1 | 6/2003 | Eichhorn et al. | |
| 2003/0144696 A1 | 7/2003 | Sinnott et al. | |
| 2003/0167072 A1 | 9/2003 | Oberlander | |
| 2003/0233107 A1 | 12/2003 | Gellman et al. | |
| 2004/0138683 A1 * | 7/2004 | Shelton | A61B 17/0401 606/151 |
| 2005/0267478 A1 | 12/2005 | Corradi et al. | |
| 2007/0043384 A1 | 2/2007 | Ortiz et al. | |
| 2007/0100352 A1 | 5/2007 | Deffenbaugh et al. | |
| 2007/0203498 A1 | 8/2007 | Gerber et al. | |
| 2009/0312772 A1 | 12/2009 | Chu | |
| 2010/0113873 A1 | 5/2010 | Suzuki et al. | |
| 2010/0222812 A1 | 9/2010 | Stone et al. | |
| 2010/0262166 A1 * | 10/2010 | Boraiah | A61B 17/34 606/148 |
| 2010/0292731 A1 | 11/2010 | Gittings et al. | |
| 2011/0112576 A1 | 5/2011 | Nguyen et al. | |
| 2011/0301699 A1 | 12/2011 | Saadat | |
| 2013/0197577 A1 | 8/2013 | Wolf et al. | |
| 2015/0066060 A1 | 3/2015 | Bojarski et al. | |
| 2015/0157309 A1 | 6/2015 | Bird | |
| 2015/0257751 A1 * | 9/2015 | Bachar | A61B 17/0401 606/148 |

FOREIGN PATENT DOCUMENTS

| | | |
|---|---|---|
| WO | 96/25102 A1 | 8/1996 |
| WO | 01/85035 A2 | 11/2001 |
| WO | 2009/126781 A1 | 10/2009 |
| WO | 2010/115113 A1 | 10/2010 |
| WO | 2011/037977 A1 | 3/2011 |
| WO | 2011/039732 A1 | 4/2011 |
| WO | 2014/018946 A1 | 1/2014 |
| WO | 2014/033692 A2 | 3/2014 |
| WO | 2014/039651 A1 | 3/2014 |
| WO | 2014/120510 A1 | 8/2014 |
| WO | 2017/006321 A1 | 1/2017 |

* cited by examiner

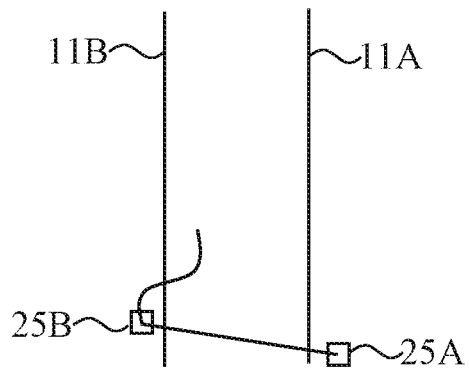
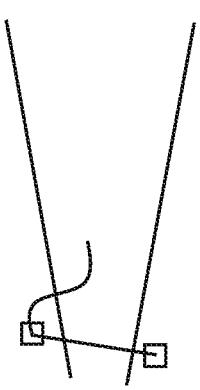
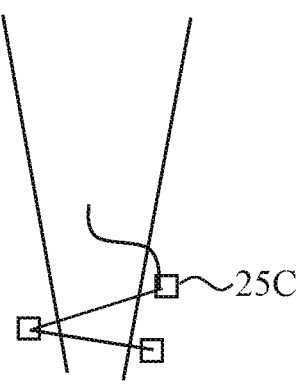
Fig. 4A  Fig. 4B  Fig. 4C
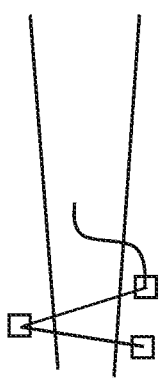
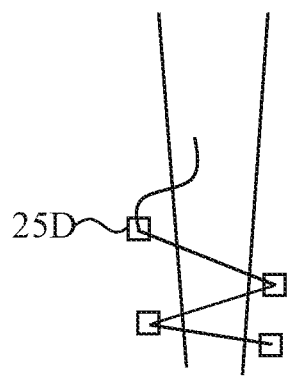
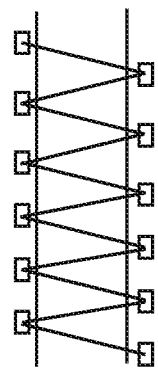
Fig. 4D  Fig. 4E  Fig. 4F

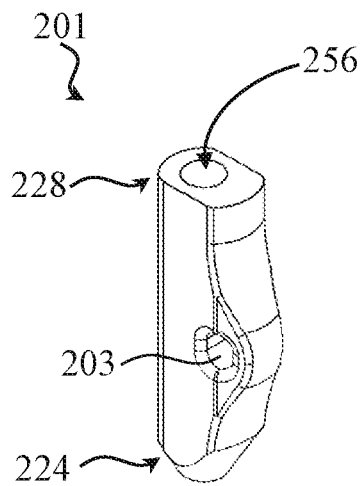
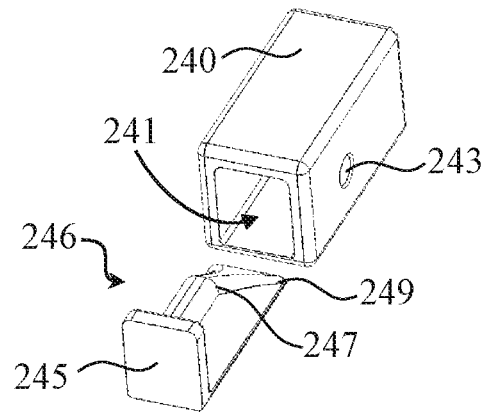
Fig. 6A          Fig. 6B
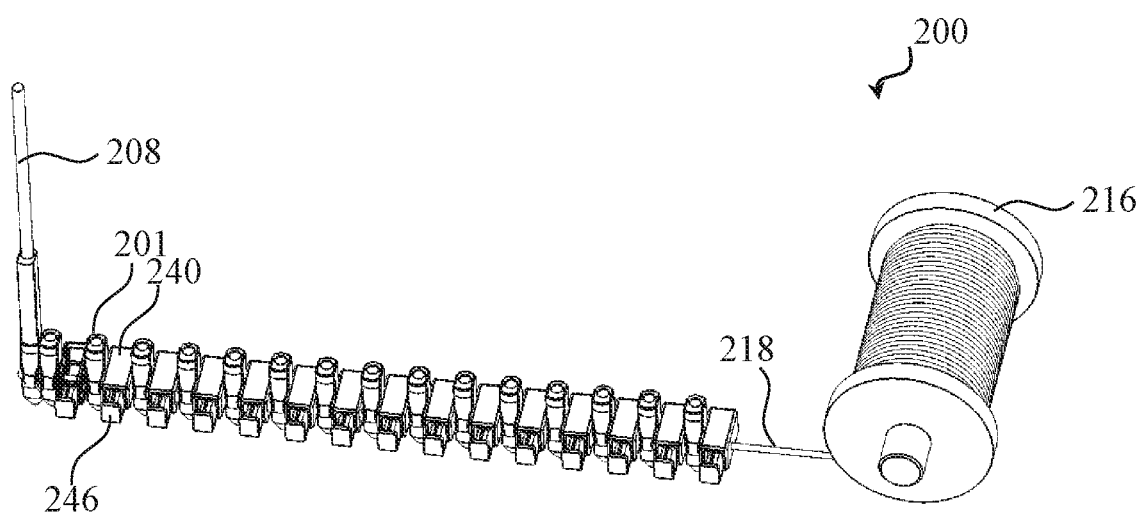
Fig. 6C

DEVICE AND METHOD FOR SUTURING

TECHNOLOGICAL FIELD

The present disclosure provides a system, a device, a cassette for use therein and method for suturing two tissue sections, for example two sections of a tissue, by using a plurality of anchoring units.

BACKGROUND ART

References considered to be relevant as background to the presently disclosed subject matter are listed below:
[1] WO 2011/039732
[2] WO 2014/033692
[3] WO 2014/039651
[4] U.S. Pat. No. 6,500,184

Acknowledgement of the above references herein is not to be inferred as meaning that these are in any way relevant to the patentability of the presently disclosed subject matter.

BACKGROUND

Suturing is used in many surgical operations to close, i.e. bring together, tissue sections which have been separated, e.g. by cutting. For example, during hernia repair or c-section surgical operations, the abdominal fascia tissue is surgically cut, and then needs to be stitched-up (or sutured together). Sutures are used in order to maintain the cut tissue sections proximal to one another during the healing period of the tissue. A growing number of post-surgical complications, typically relating to suture slaking due to tension unevenly distributed in the suture thread, due to tearing of the thread and/or disengagement of the thread from the sutured tissue, pose significant risks to the patients' health and often require additional surgical involvement. Such post-surgical complications are also of great concern to care-takers and medical insurance organizations due to the costs associated with such secondary surgical involvement and post-surgical treatments.

Traditional suturing involves using a needle threaded with a suitable suturing thread, that is operated by the surgeon by hand or by using forceps. The needle is passed through both tissues sections, and the thread is pulled to bring the tissue sections into proximity. During traditional fascia suturing procedure, a single, continuous thread is used and the needle is consecutively passed through both tissue sections in order to obtain a single, continuous suture. The suture is secured at both ends by a knot. Such traditional suturing procedures typically require the involvement of at least two surgical staff members, one member for holding the tissue sections to be sutured in proper orientation with respect to one another, and the other staff member for performing the suturing procedure. As a single thread is used, there is a risk of the suture tearing during the procedure. In addition, due to the thickness of the fascia tissue layer and the relatively high force required to pass the needle through it, surgeons often suffer from needle pricks during surgery that may pose a health risk and exposure to contaminations to both the surgeon and the patient. Further, due to uneven tensioning or slaking of the thread, ischemic damage in vicinity to the suture may be formed.

Some alternative devices and suturing methods have been proposed in the art. One of the common techniques used is stapling, in which the tissue sections are held in proximity to one another by metal staples. Although stapling is a procedure that is quicker than traditional suturing, it is unsuitable for holding together thick tissues and is, thus, used in cosmetic or superficial skin incisions (i.e. incisions that are not carried out in the deep-tissue).

Another technique involves using multiple single stitches instead of a continuous suture. This may be accomplished by passing the needle through the first and second tissue sections, and tying (or locking) the thread to form a single, individual, suture after each such passing. The thread is then cut, and other such single sutures are similarly applied until the tissue sections are stitched together. Such application of a plurality of single stitches may be carried out manually by the surgeon, or applied by using a dedicated device, such as that described in [1]. In this suturing technique it is difficult to obtain uniformity in the size of sutures and/or an even distribution of stresses along the sutured tissue. Moreover, the individual knots are often bulky, causing inconvenience to the patient. In addition, the plurality of exposed thread edges (resulting from the multiple cutting of the thread to form individual sutures) may cause local irritation and/or sites of infection in the tissue.

A similar procedure involves applying anchoring members, passing through the tissue sections, such that the anchoring members are fixed within the tissue and the thread is passed between pairs of anchoring members, the first being fixed to one section of the tissue and the other being fixed to the opposite tissue section. The thread is then tied or locked in position, to form singular sutures, each constituted by a pair of anchoring members and a respective thread linking between them. Typical devices are disclosed, for example in [2-4].

GENERAL DESCRIPTION

The present disclosure provides a system, a device and a method for suturing two tissue sections, in particular, but not limited to, two sections of fascia, thoracic wall, thick muscular tissue, etc. By the current disclosure anchoring units are alternately fixed in opposite tissue sections and then one or more threads, that are a priori linked to the anchoring units, are manipulated to thereby bring a deployed unit into proximity with a previous deployed unit; namely a first of the plurality of anchoring units is brought into proximity with a second, the second with a third, the third with a fourth, etc. Thus, according to this disclosure, suturing by deploying consecutive anchoring units is a procedure with at least two steps: in a first step the anchoring elements of the anchoring units are inserted into and secured within the tissue (each anchoring unit is secured into an opposite tissue section to a previous unit); and then, in a second step, the one or more threads, which a priori linked to coupling elements of the anchoring units that remain outside the tissue, is manipulated to bring the two consecutive anchoring units into proximity, which in turn brings the two opposite tissue portions into proximity. The coupling elements are them locked into position, thereby resulting in locking of consecutive anchoring units in position one with respect to the other.

By an embodiment of this disclosure, a plurality of the first steps are first carried out, followed by a plurality of the second steps; namely a plurality of anchoring units are alternately inserted and secured in opposite tissue sections and only then the thread is manipulated to bring consecutive anchoring units, and hence opposite tissue portions, into proximity. By another embodiment, the second step immediately follows the first step for bringing a deployed unit into proximity with a previous deployed unit; namely once a consecutive anchoring unit is fixed in position in a second tissue section (the previous anchoring unit being already fitted in the first tissue section), the thread is manipulated to bring two consecutive anchoring units and hence respective tissue portions of the first and the second opposite tissue sections into proximity; and only then a subsequent consecutive anchoring unit is inserted and fixed in the first tissue section and the same sequence of steps being repeated.

Also provided by this disclosure is a cassette of anchoring units, of the kind specified, for use in said device.

In this disclosure the term "consecutive" is being used to refer to anchoring units that are intended for insertion into tissue sections to be sutured serially one after the other: a second of such consecutive units after a first, a third after a second, etc.

At times, the term "first" and "second" are used to designate one of the opposite tissue section to be sutured. These designations have no functional significance and are used only for simplifying the description.

The term "tissue section" is used to refer to two tissue parts that are intended for suturing. Such sections may for example be sections of fascia surgically cut in an abdominal or chest surgery. The term "tissue portion" when used in relation to the tissue denotes part of a tissue section that is in the vicinity of the anchoring unit, and intended to be engaged thereby, and hence being forced against an opposite portion by forcing (through pulling or tensioning of the thread) consecutive units towards one another.

The term "thread" is used to denote any type of cord or thread that can be linked to the coupling elements of the anchoring units. It may be made of any one of a variety of suitable materials (e.g., biodegradable or not biodegradable), of any thickness or cross-section, may be smooth, structured or textured (e.g. textured such as to permit unidirectional relative movement of the thread with respect to the coupling element in a direction that increases tensions in the thread due to the pulling of two opposite tissue portions towards each other), etc.

The term "suture" or "suturing" is used herein to refer to the surgical operation of closing and bringing together opposite tissue sections that have been surgically cut or otherwise ruptured. This term encompasses, in particular, the method of tissue closing, which may be carried out by the device in accordance with the disclosure, although it may not fall within the classical meaning of the term "suturing".

Provided by one aspect of this disclosure is a system and a device for suturing together two tissue sections. The system comprises an arrangement of a plurality of consecutive anchoring units intended for deployment in a tissue to be sutured. In the device, such an arrangement is held in a suitably-configured holder (which is typically, but not exclusively, in the form of a cassette described hereinbelow). The units are linked to one another by one or more suturing threads (typically by one continuous thread), each unit comprises a tissue-anchoring element ("anchoring element") and a thread-coupling element ("coupling element") which is coupled to the thread. The two elements in each unit are linked to one another: the link may be a rigid association whereby the coupling element and the anchoring element constitute in fact one integral anchoring unit; or the two may be linked to one another by a flexible or pliable link, in particular such a link being formed by one or more of the suturing threads, in a manner to be illustrated further below.

Each of the anchoring elements is configured for penetration through the tissue, and for deployment in the tissue after penetration into the tissue, in a manner so as to arrest the anchoring element from retracting back from the tissue. Thus, the anchoring element has a deploying state and a deployed state, and is switchable between the two upon penetration into the tissue. The one or more threads are slidably coupled to the coupling element, and extend between the coupling elements of consecutive anchoring units. Consequently, manipulation of the threads, in particular tensioning of the thread, brings a deployed unit (namely, a unit having its anchoring element anchored within the tissue) into proximity with another previously deployed anchoring unit.

The coupling element is configured for locking to the suturing thread once consecutive anchoring units are brought into proximity. Such locking may be by means of coupling between the coupling element and the one or more threads in a manner that permits only one directional movement of the thread relative to said coupling element; or the locking may be achieved through use of an auxiliary locking member fitted into said coupling element, such that fitting the auxiliary locking member into the coupling element, typically after the thread has been tensioned, locks the thread in its tensioned state. In the latter embodiment that makes use of an auxiliary locking member, the device typically holds a series of auxiliary locking members corresponding to the anchoring units. In other embodiments, the coupling element is integral with the auxiliary locking element, such that insertion of the auxiliary locking element into the coupling element causes locking of the thread in the tensioned state.

The device also comprises an actuation arrangement that is configured for deploying the anchoring unit into the tissue, such that the anchoring unit becomes fixed within the tissue. The actuation arrangement also permits manipulation of the thread to bring the deployed unit into said proximity with the previously deployed unit.

By one embodiment of this disclosure, the actuation arrangement comprises a displacing member axially reciprocating in a forward-rearward direction (forward direction being toward the tissue and rearward being away from the tissue) and configured to thereby displace the anchoring unit (or a tissue-penetrating portion thereof) to a position in which the anchoring element is fixed within the tissue. Said displacing member has typically an elongated forward portion, that is defined between a tapered tissue-penetrating end and a shoulder. The tissue-penetrating portion of the anchoring unit is in such a case provided with an axial bore dimensioned to receive the forward portion of the displacing member, permitting the forward position of the displacing member to pass through the bore, but not permitting passage of the shoulder. The length of the bore is such, that once the forward portion is fully received therein, the tapered end of the forward position forwardly extends from the front end of the bore. The displacing member in the device is accordingly configured for insertion of said forward portion through said bore to thereby axially displace said tissue-penetrating portion into the tissue, the tapered end of the displacing member providing penetrating passage for insertion of the anchoring element (or portion thereof) into the tissue.

The anchoring units, by some embodiments, are configured to define a tissue penetration axis between a first, tapered end portion forwardly directed toward the tissue and a second, opposite end; the anchoring element is fitted at the first end portion and the coupling element at the opposite end portion of the anchoring unit. The actuation arrangement in such a case is thus configured for axial, forward displacement of the anchoring element into the tissue.

In another embodiment, the anchoring unit itself comprises a tissue-penetrating shaft that axially extends between a first, tapered end portion and a second, opposite end portion, with the anchoring elements (for example configured as flaps) are formed at said first end portion, the anchoring elements (e.g. flaps) being switchable between a deployment state in which they are flush with the surface shaft's first end portion and a deployed state, and biased into the latter state in which they extend in the radial direction away from said surface to thereby arrest retraction of the shaft back from the tissue. The coupling element may then be associated with the shaft in an axially slidable manner, wherein, during displacement, the shaft axially slides with respect to the coupling element until such relative movement brings the coupling element to be at the second end of the shaft. This slidable displacement is typically afforded by means of a bore defined in the coupling element, with the shaft fitting into and sliding axially within said bore. The shaft is typically provided with an arresting element to arrest the relative axial displacement of the coupling element vis-à-vis the shaft at said second end.

The bringing together of consecutive anchoring units is against a strong bias of the tissue and requires tensioning of the thread. Once tensioned to bring the anchoring units into proximity, the thread needs to be locked by the coupling element to keep the opposite tissue sections adjacent one another. This may be achieved by tailoring the coupling element (and optionally also the thread) to permit a locking interaction between the thread and the coupling element. Arrangements that permit such interaction are, for example, engagement between a jagged suturing thread and a complementary jagged surface of the bore through which the thread passes in the coupling element. Another example is a ratchet mechanism, which allows relatively free pulling in a thread-tensioning direction and blocking movement in the opposite, tensioning-release direction. The thread tensioning mechanism in the device may include a tension-release mechanism (that may also be adjustable by the physician user) to permit tensioning of the thread on the one hand but avoid excessive tension (tissue which may cause ischemia or other tissue damages) on the other hand. Such a tensioning mechanism may be mechanical, electrical, etc. Also, the coupling and locking mechanism may be tailored to have a locking-breaking threshold to avoid such excessive tension if applied during deployment or formed subsequent thereto. The device may further comprise a gage or an indicator that provides the practitioner with an indication of the tension applied onto the thread and/or a warning that excessive tension is applied.

The device may further comprise, by one embodiment, a thread-cutting mechanism for cutting the thread at the end of the suturing procedure.

By one embodiment, the anchoring element is an independent element linked to the coupling element by one or more of the threads. In this embodiment, the anchoring element is inserted into the tissue, the coupling element is fitted at the tissue's exterior and the thread passing between them, after being tensioned, links and holds the two together. The same tensioning action or an additional one then brings the anchoring unit into said proximity with the previously deployed anchoring unit. The anchoring unit may be configured with a first tapered end which permits its insertion into the tissue by axial displacement of the anchoring unit into the tissue.

By another embodiment, the anchoring unit is provided with an axial bore and is deployed into the tissue by the use of a displacing member of the kind having an elongated forward portion, with a tapered tissue-penetrating end of the kind described above.

By one embodiment, such an independent anchoring element is generally elongated along an axis with a thread-engaging member at a mid-portion. The anchoring element of this embodiment is axially inserted into the tissue and once passing through the tissue, pulling the thread causes the anchoring element to orient into a lateral orientation with a thread passing through the passage created by the displacing member. The anchoring element is linked to the coupling element at the tissue's exterior, with the anchoring element being arrested within the tissue by its lateral orientation, and the coupling element is then locked.

The one or more threads are arranged such that once two consecutive anchoring units are extracted, suitable manipulation of the thread brings the two consecutive units into proximity to one another. The actuation arrangement is configured for extracting a first-in-line of the consecutive anchoring units out of the device's and deploying it.

The term "first-in-line" refers to the anchoring unit within the device that will be the one to be deployed upon actuation. This is either the first of the consecutive anchoring units or a first of the remaining anchor units that remain within the device after the extraction of a previous one (i.e. the first of the anchoring members remaining in the device that is next to be extracted).

The anchoring units and their elements may be made of any suitable material, e.g. metal, plastic or other polymeric material. In some embodiments, the anchoring units or at least the anchoring elements are made of or comprise a biodegradable material.

It is of note that, compared to the suture thread passing through the tissue in classic suturing techniques, the anchoring elements have a larger surface in contact with the tissue (as compared to the surface contacted by the suturing thread in classic techniques), which may reduce the likelihood of the development of ischemic damage and/or the risk to hernia formation in the scar area.

The device may be preloaded with a predefined number of anchoring units, and provided as such. Such a preloaded device may, by one embodiment, be disposable and intended for use in a single suturing procedure. In such embodiments, the device may be made of a recyclable or degradable material. In other embodiments, the device may be designed for multiple uses, and may be made out of construction materials that permit sterilization (for example by an autoclave). When configured for multiple uses, the device's holder is typically designed to hold a replaceable, cassette, or cartridge that holds the arrangement of the plurality of anchoring members, such that once such a cassette is inserted into the receptacle, the actuation arrangement can controllably drive the anchoring units from the cassette one at a time upon actuation into a tissue portion.

Such a cassette constitutes an independent aspect of this disclosure. The cassette comprises a plurality of consecutive anchoring units, of the kind described above. The one or more threads are coupled to the coupling elements of the anchoring units and are arranged such that, once consecutive anchoring units are extracted and fixed in operable position with respect to opposite tissue portions, manipulation of the thread brings the consecutive units and, therefore, the opposite tissue portions, into proximity to one another. The anchoring units are arranged in said cassette to permit extraction of a first-in-line anchoring unit and axially displacing the unit into the tissue.

By some embodiments the one or more threads pass through the coupling elements of all anchoring units (and optionally also through all of the anchoring elements). In other embodiments, the a continuous thread linked between all of the coupling elements.

As the tissue to be sutured may vary in thickness from patient to patient, anchoring units having different dimensions, i.e. having shafts of different lengths and/or diameters, may be used. Once assessing the thickness of the tissue to be sutured, the practitioner may then load the proper units into the device or chose the proper device with properly dimensioned pre-loaded anchoring units.

According to another aspect, provided is a kit, comprising the device or system of this disclosure and one or more cassettes (e.g. a plurality of cassettes each holding anchoring units of different dimensions) as herein defined.

Provided by another aspect of this disclosure is method for suturing together a first and second opposite tissue sections. The method of this disclosure comprises providing a plurality of consecutive anchoring units linked to one another by one or more suturing threads; deploying each anchoring unit in said plurality into the tissue section, wherein each of the anchoring units is deployed in an opposite tissue section to that of a previous unit; manipulating the thread to tension it brings consecutive anchoring units into proximity one to the other; and locking the thread in a tensioned state.

Each of the anchoring units comprises a tissue-anchoring element and a thread-coupling element coupled to the thread, the two elements in each unit being linked to one another. Each anchoring element is configured for penetration through the tissue and for deployment after tissue penetration in a manner so as to arrest said anchoring element from retracting back through the tissue. The one or more threads are slidably coupled to the coupling elements and extending between coupling elements of consecutive anchoring units. The coupling elements are configured for locking the suturing thread.

By an embodiment of this disclosure, the manipulation of the thread is through pulling at least one portion of the thread. This may be through displacement of the thread with respect to at least one of the consecutive anchoring units. The manipulation of the thread to bring consecutive anchoring units into proximity to one another may be through an actuation arrangement of the device or may be by direct manipulation of the thread, e.g. by forceps.

It is of note that the system, device and method described herein enable a continuous suturing process, thereby significantly simplifying, and/or reducing the duration of the suturing procedure. Further, the device and method described herein may increase surgeon safety (e.g. avoiding unintentional pricking). By one embodiment, after one anchoring unit is fixed in a tissue section, a consecutive anchoring unit is fixed into the opposite section. The thread is then manipulated to cause tension to bring this pair of units, and hence the respective two tissue portions, into proximity. This procedure is repeated for the entire length of the section with the aforementioned "consecutive" becoming said "previous" anchoring unit for the subsequent step of the procedure. This enables the provision of a continuous suturing while securing each anchoring unit to the a consecutive or previously anchoring unit.

By another embodiment, the tensioning of the thread between each pair is carried out after all anchoring units are fixed into the two opposite tissue sections.

Thus, in accordance with this disclosure, consecutive anchoring units are tightened independently against one another; namely the second against the first, the third against the second, the fourth against the third, etc. This serves to distribute the load and also, a failure of this link between two consecutive anchoring units (for whatever reason) will have a minimal and possibly negligible effect on the integrity of the entire suture. For example, when one link between two consecutive anchoring units is ruptured, i.e. due to tearing of the thread, this will have only local effect on the integrity of the suture; the engagement of the thread with the rest of the anchoring units ensures that no slacking of the thread occurs and a negligible effect on the tension distribution along the suture is obtained.

Use of the system, device and/or method of this disclosure for suturing two opposite fascia section, e.g. sections separated by a surgical cut, is one specific embodiment of this disclosure. In a suturing procedure according to this embodiment, a first anchoring unit is inserted and secured into one fascia section and a subsequence unit into the other fascia section. The anchoring units of this embodiment are, thus dimensioned for penetrating through the fascia and deployed at the fascia's interior. Another embodiment is use of the system, device or method of this disclosure in minimal invasive surgical (MIS) procedures.

EMBODIMENTS

In the following, embodiments of this disclosure are described by means of numbered embodiments. These numbered embodiments are intended as an addition to the above disclosure and are not limiting.

1. A device for suturing together two tissue sections, comprising:

a holder holding a plurality of consecutive anchoring units for deployment in a tissue, the units being linked to one another by one or more suturing threads, each comprising a tissue-anchoring element and a thread-coupling element coupled to the thread, the two elements in each unit being linked to one another;

each anchoring element being configured for penetration through the tissue and for deployment after tissue penetration in a manner so as to arrest said anchoring element from retracting back through the tissue;

the one or more threads being slidably coupled to the thread-coupling element and extending between thread-coupling elements of consecutive anchoring units, such that manipulating the thread brings a deployed unit into proximity with a previous deployed unit;

the thread-coupling elements being configured for locking to the suturing thread once brought into said proximity; and comprising an actuation arrangement configured for deploying an anchoring unit such that the anchoring element is fixed into the tissue, and for manipulating the thread to bring a deployed unit into said proximity 2. The device of embodiment 1, wherein the actuation arrangement comprises a displacing member axially reciprocating in a forward-rearward direction and configured for displacement of the anchoring unit or tissue-penetrating portion thereof to position the anchoring element within the tissue.

3. The device of embodiment 2, wherein said displacing member has an elongated forward portion defined between a tapered, tissue-penetrating end and a shoulder, said tissue-penetrating portion has an axial bore dimensioned to receive said forward portion and permitting it to pass therethrough but not permitting passage of said shoulder, such that once fully received the tapered end of said forward portion forwardly extends from a front end of the bore, said displacing member being configured for insertion of said forward portion through said bore, to thereby axially displace said tissue-penetrating portion into the tissue with said tapered end providing a tissue-penetrating passage therefor.

4. The device of any one of embodiments 1-3, wherein each anchoring unit defines a tissue penetration axis between a first, tapered, end portion forwardly directed and between second, opposite end portion; the anchoring unit being fitted at said first end portion and the coupling element being at the opposite, second end portion; the actuation arrangement configured for forward, axial displacement of said unit into the tissue.

5. The device of any one of embodiments 1-3, wherein the anchoring unit comprises a tissue-penetrating shaft axially extending between a first, tapered end portion and a second, opposite end portion, an anchoring element at said first end portion configured as flaps switchable between a deployment state in which they are flush with the surface of the shaft's first end portion and a deployed state and biased into the latter state in which they extend in the radial direction away from said surface to thereby arrest retraction of the shaft back through the tissue, and a coupling element associated with the shaft in an axially slidable manner.

6. The device of embodiment 5, wherein the actuation arrangement is configured to axially displace said shaft into the tissue.

7. The device of embodiment 5, wherein during displacement the shaft axially slides within an a bore defined by the coupling element whereby after deployment the coupling element is positioned at said second end portion.

8. The device of embodiment 7, wherein the shaft has an arresting element to arrest the relative axial displacement of the coupling element vis-à-vis the shaft at said second end.

9. The device of embodiment 7 or 8, wherein in operation the coupling element is made to rest against the tissue and said shaft is axially displaced into the tissue through said bore.

10. The device of embodiment 9, configured for fitting an auxiliary locking member into said coupling element to lock the thread in its tensioned state.

11. The device of embodiment 10, comprises a series of consecutive auxiliary locking members corresponding to the anchoring units.

12. The device of any one of the preceding embodiments, wherein the coupling element is in rigid association with the anchoring element of the same unit to define together the anchoring unit.

13. The device of embodiment 12, wherein the coupling element is integral with the anchoring element to define together an integral anchoring unit.

14. The device of any one of the preceding embodiments, wherein the anchoring element and the coupling element elements of a unit are linked to one another by the one or more suturing threads.

15. The device of embodiment 14, wherein after anchoring the anchoring element within the tissue the portion of the thread between the anchoring element and the coupling element is tensioned.

16. The device of embodiment 14 or 15, wherein the one or more threads are slidably coupled to the anchoring element.

17. The device of any one of the preceding embodiments, wherein the manipulation of the thread is through pulling at least one portion thereof.

18. The device of any one of the preceding embodiments, for suturing together opposite fascia sections, wherein each first of two consecutive anchoring units is intended for fitting into one fascia section and the second of two consecutive anchoring units is intended for fitting into the opposite fascia section.

19. The device of embodiment 18, wherein the anchoring units are dimensioned for penetrating through the fascia with the anchoring element being deployed at the fascia's interior.

20. The device of any one of the preceding embodiments, wherein the holder is configured as a receptacle for receiving a cassette that comprises said plurality of consecutive anchoring units.

21. The device of any one of the preceding embodiments, wherein the coupling element is coupled to the one or more threads in a manner permitting one-directional movement of the thread relative said coupling element.

22. The device of any one of the preceding embodiments, wherein said one or more threads comprises a single thread passing through the coupling elements of all anchoring members.

23. The device of any one of the preceding embodiments, wherein the actuation arrangement comprises a compressible handle.

24. A tissue suturing system for suturing together two tissue sections, comprising:

an arrangement of a plurality of consecutive anchoring units for deployment in a tissue, the units being linked to one another by one or more suturing threads, each comprising a tissue-anchoring element and a thread-coupling element coupled to the thread, the two elements in each unit being linked to one another;

each anchoring element being configured for penetration through the tissue and for deployment after tissue penetration in a manner so as to arrest said anchoring element from retracting back through the tissue;

the one or more threads being slidably coupled to the thread-coupling element and extending between thread-coupling elements of consecutive anchoring units, such that manipulating the thread brings a deployed unit into proximity with a previous deployed unit;

the thread-coupling elements being configured for locking to the suturing thread once brought into said proximity; and comprising an actuation arrangement configured for deploying an anchoring unit such that the anchoring element is fixed into the tissue, and for manipulating the thread to bring a deployed unit into said proximity.

The device features of embodiments 2-23 are also features of embodiments of the system, generally describes in embodiment 24. For the sake of brevity, these will not be repeated, but it should be understood that system embodiments corresponding to the device embodiments 2-23 are also encompassed by this disclosure. Thus, this disclosure encompasses also a system with the general features as define in embodiment 24, with additional features as described in any of embodiments 2-23.

25. A cassette for a suturing device, comprising a plurality of consecutive anchoring units for deployment in a tissue, the units being linked to one another by one or more suturing threads, each comprising a tissue-anchoring element and a thread-coupling element coupled to the thread, the two elements in each unit being linked to one another;

each anchoring element being configured for penetration through the tissue and for deployment after tissue penetration in a manner so as to arrest said anchoring element from retracting back through the tissue;

the one or more threads being slidably coupled to the thread-coupling element and extending between thread-coupling elements of consecutive anchoring units, such that manipulating the thread brings a deployed unit into proximity with a previous deployed unit;

the thread-coupling elements being configured for locking to the suturing thread once brought into said proximity;

the anchoring units being arranged in said cassette to permit manipulation of a first-in-line anchoring unit for inserting the anchoring element into the tissue.

26. The cassette of embodiment 25, wherein each of the anchoring units has a tissue-penetration portion with an axial bore.

27. The cassette of embodiment 25 or 26, wherein each anchoring unit defines a tissue penetration axis between a first, tapered, end portion forwardly directed and between second, opposite end portion; the anchoring unit being fitted at said first end portion and the coupling element being at the opposite, second end portion.

28. The cassette of any one of embodiments 25-27, wherein each anchoring unit has a tissue-penetrating shaft axially extending between a first, tapered end portion and a second, opposite end portion, an anchoring element at said first end portion configured as flaps switchable between a deployment state in which they are flush with the surface shaft's first end portion and a deployed state and biased into the latter state in which they extend in the radial direction away from said surface to thereby arrest retraction of the shaft back through the tissue, and a coupling element associated with the shaft in an axially slidable manner.

29. The cassette of embodiment 28, wherein during displacement the shaft axially slides within an a bore defined by the coupling element whereby after deployment the coupling element is positioned at said second end portion.

30. The cassette of embodiment 29, wherein the shaft has an arresting element to arrest the relative axial displacement of the coupling element vis-à-vis the shaft at said second end.

31. The cassette of embodiment 29 or 30, wherein in operation the coupling element is made to rest against the tissue and said shaft is axially displaced into the tissue through said bore 32. The cassette of any one of embodiments 28-31, comprising a series of consecutive locking members corresponding to the anchoring units for fitting into said coupling element to lock the thread in its tensioned state.

33. The cassette of any one of embodiments 25-32, wherein the coupling element is in rigid association with the anchoring element of the same unit to define together the anchoring unit.

34. The cassette of embodiment 33, wherein the coupling element is integral with the anchoring element to define together an integral anchoring unit.

35. The cassette of any one any one of embodiments 25-34, wherein the anchoring element and the coupling element of a unit are linked to one another by the one or more suturing threads.

36. The cassette of embodiment 35, wherein the one or more threads are slidably coupled to the anchoring element.

37. The cassette of any one of embodiments 25-36, wherein the anchoring units are dimensioned for penetrating through fascia with the anchoring element being deployed at the fascia's interior.

38. The cassette of any one of embodiments 25-37, wherein the coupling element is coupled to the one or more threads in a manner permitting one-directional movement of the thread relative said coupling element.

39. The cassette of any one of embodiments 25-28, wherein said one or more threads pass through the coupling elements of all anchoring members.

40. The cassette of any one of embodiments 25-39, for use in a device of any one of embodiments 1-23 or the system of embodiment 24 or any of the other system embodiments with features corresponding to those of embodiments 2-23.

41. A kit comprising the device of any one of claims 1-23 or the system of embodiment 24 or any of the other system embodiments with features corresponding to those of embodiments 2-23, and at least one cassette as defined in any one of embodiments 25-39.

42. A method for suturing together a first and second opposite tissue sections, comprising:

providing a plurality of consecutive anchoring units linked to one another by one or more suturing threads, each of the units comprises a tissue-anchoring element and a thread-coupling element coupled to the thread, the two elements in each unit being linked to one another, each anchoring element being configured for penetration through the tissue and for deployment after tissue penetration in a manner so as to arrest said anchoring element from retracting back through the tissue, the one or more threads being slidably coupled to the thread-coupling element and extending between thread-coupling elements of consecutive anchoring units, the thread-coupling elements being configured for locking the suturing thread;

deploying each of the plurality of anchoring units into the tissue section, wherein each of the anchoring units is deployed in an opposite tissue section to that of a previous unit;

manipulating the thread to tension it bring each two consecutive anchoring units into proximity one to the other; and locking the thread in a tensioned state.

43. The method of embodiment 42, wherein said manipulating comprises pulling at least a portion of the thread.

44. The method of embodiment 42 or 43, for suturing together two fascia sections.

45. A device for carrying out the method of any one of embodiments 42-44.

BRIEF DESCRIPTION OF THE DRAWINGS

In order to better understand the subject matter that is disclosed herein, understand the features that distinguish it from the art and exemplify how it may be carried out in practice, embodiments will now be described, by way of non-limiting example only, with reference to the accompanying drawings, in which:

FIGS. 4A-4F are schematic representations of steps of a suturing procedure according to an embodiment of the invention.

FIG. 6A shows, in isolation, an anchoring element according to another embodiment of this disclosure.

FIG. 6B shows, in isolation, a coupling element according to another embodiment of this disclosure.

FIG. 6C shows a system of anchoring units, according to another embodiment of the invention.

DETAILED DESCRIPTION OF EMBODIMENTS

In the following description, some of the novel features of this disclosure will be illustrated with respect to certain embodiments. This description, as can be appreciated, is intended to illustrate the entire scope of the invention, as defined above, and is not intended to be limiting. Furthermore, these embodiments will be described with respect to suturing of cut fascia sections. As can be appreciated, the invention is not limited to fascia and may apply to suturing of other tissue sections in surgical procedures other than such involving cutting through fascia.

Figure 1A:
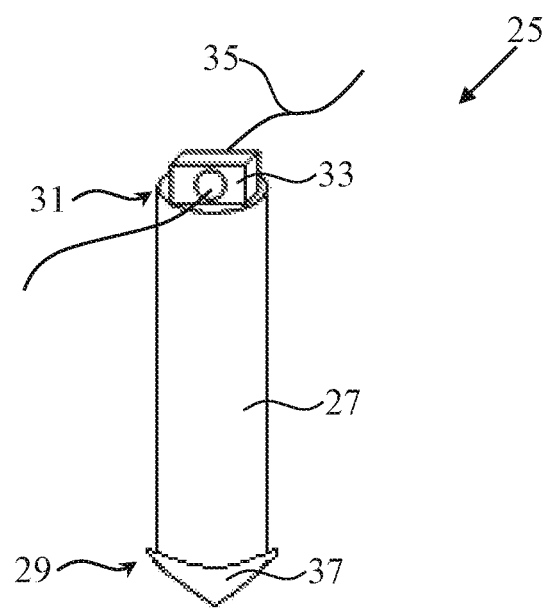
FIGS. 1A and 1B show, in respective deployment and deployed configurations, an anchoring unit, in accordance with an embodiment of this disclosure.
Figure 1B:
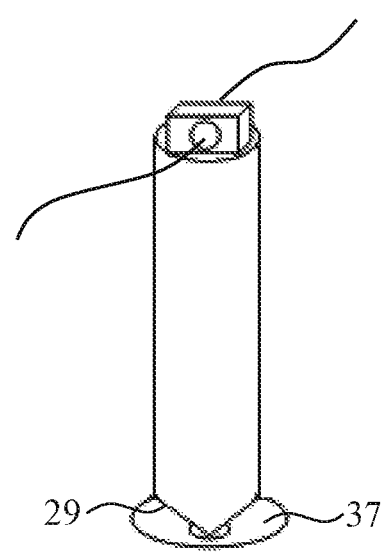

In accordance with this disclosure, anchoring units are used, which may, by one embodiment be the kind of anchoring unit 25, illustrated in FIGS. 1A and 1B. Anchoring unit 25 has a shaft 27, axially extending between a first tapered end portion 29, and a second end portion 31 that is provided with a coupling element 33 configured for coupling to a thread 35. The first end 29 comprises an anchoring element 37 that has a tissue penetration configuration, as for example illustrated in FIG. 1A, in which, e.g., it is held against the tapered end 29, and a deployed configuration illustrated in FIG. 1B. The anchoring element 37 is biased to assume the deployed configuration and, consequently, once it penetrates through the tissue, the securing element opens to thereby arrest the anchoring unit in position within the tissue by preventing the anchoring unit to be pulled back through a tissue portion when a tensioning force is applied on the thread. The tapered end 29 permits penetration of the anchoring unit 25 through and insertion within a tissue section, the insertion being through an axially applied penetration force to thereby induce the anchoring unit to penetrate axially through the tissue to its substantially entire length (or at least until anchoring element 37 passes entirely through the tissue to permit its deployment). The penetration configuration assumed by the anchoring element 37 during penetration may be so assumed through interaction with surrounding tissue portions during penetration.

Figure 2A:
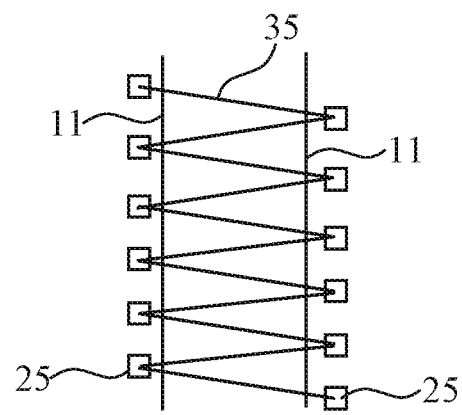
FIG. 2A is a schematic representation of a fascia suturing solution according to an embodiment of this disclosure.
Figure 2B:
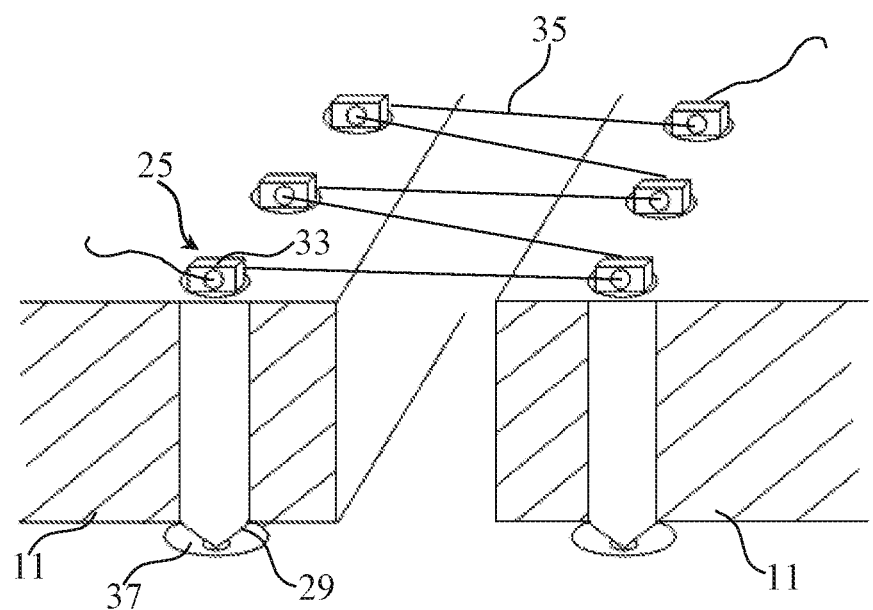
FIG. 2B is a schematic perspective and partial cross-sectional view of the suturing solution, according to said embodiment.

FIG. 2A schematically illustrates a suture passing through two opposite fascia sections in a procedure carried out according to this disclosure. A plurality of anchoring units 25 are fitted into opposite tissue sections, the boundaries of which are schematically represented by lines 11, these then being linked by a continuous thread 35 that passes through the units' coupling elements. The interaction of the thread 35 with the coupling elements 33 is such that the thread section between of consecutive anchoring units 25 may be manipulated to separately tension this section, independently of sections between other consecutive units. A more detailed illustration of this arrangement is schematically shown in FIG. 2B.

The interaction between thread 35 and the coupling element 33 may, for example, be such to allow only for unidirectional sliding of the thread vis-à-vis the coupling element or a number of other arrangements.

Figure 2C:
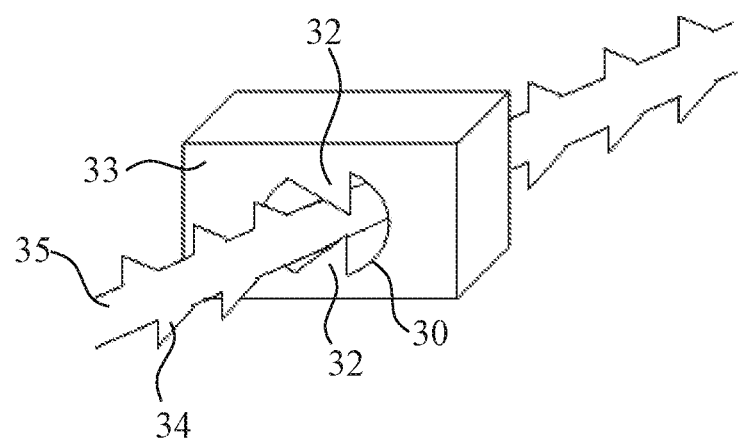
FIG. 2C is a schematic representation of an exemplary unidirectional sliding arrangement.

One, non-limiting, example of such an arrangement is shown in FIG. 2C. In FIG. 2C, bore 30 in coupling element 33 is designed to form an inner cavity extending along the bore and having a jagged cross-sectional profile, e.g., formed by wedge-like teeth 32 extending inwardly into bore 30. The thread 35, passing through bore 30, is structured with a plurality of complementary wedge-like teeth 34 extending radially from thread's outer surface. The complementary teeth 34 are designed in a manner permitting their engagement with teeth 32 of the bore, such that only a unidirectional movement of the thread is enabled through the bore 30. In this manner, the thread is controllably coupled with the coupling element, and may be tensioned to the desired tension by pulling the thread.

Figure 3A:
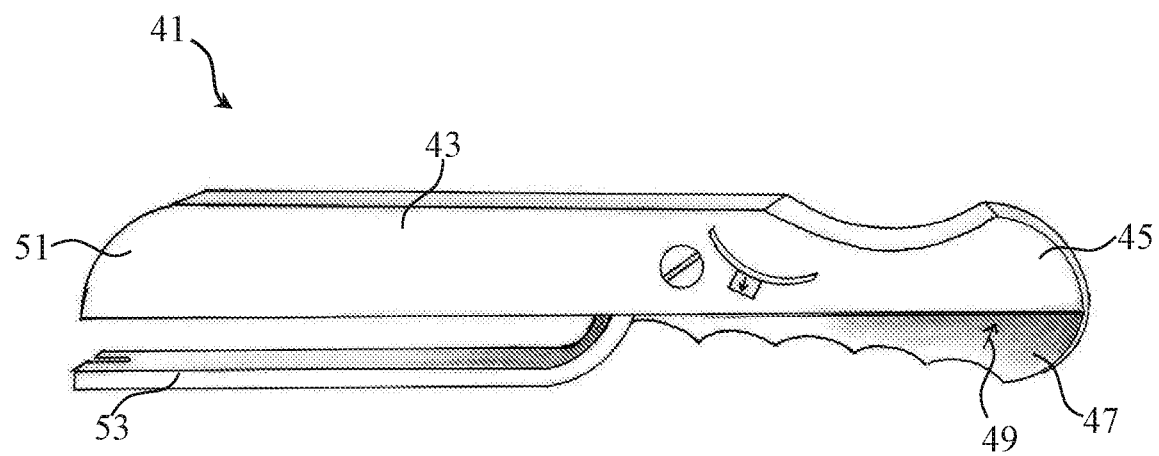
FIG. 3A is a side perspective elevation of a suturing device, according to an embodiment of this disclosure.
Figure 3B:
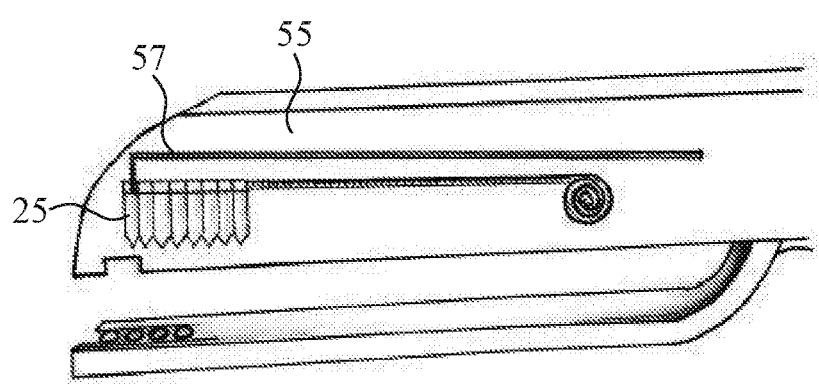
FIG. 3B shows the device of FIG. 3A in partial cross-section.

A suturing device according to an embodiment of this disclosure is schematically shown in FIGS. 3A and 3B. Device 41 has a body 43 with rear grip portion 45 housing an actuation lever 47 that can be pressed in the direction represented by arrow 49. The front end 51 is fitted with a tissue guide 53 which, while suturing, is positioned against the fascia's inner part to provide support permitting axial insertion of the anchoring unit 25. A plurality of anchoring units 25 is housed in an appropriate receptacle 55 within the front section 51 of the device. Pressing lever 47 actuates member 57 to extract an anchoring unit and axially push or drive it through an underlying tissue portion.

A suturing procedure according to an embodiment of this disclosure is schematically illustrated in FIGS. 4A-4F. A first anchoring unit 25A is first driven into a first tissue section 11A and then another, consecutive anchoring unit 25B is driven into the opposite tissue section 11B. The thread section 35A extending between units 25A and 25B is then tensioned, whereby the respective tissue portions in the two opposite sections are then brought into proximity with one another, as illustrated in FIG. 4B, compared to the anchor's initial position before tension was applied on the thread. Then the next consecutive unit 25C is inserted into tissue section 11A the procedure is repeated, as illustrated in FIGS. 4C and 4D; and then further anchoring unit 25D is inserted into tissue section 11B, and so forth until achieving a final suture, as schematically illustrated in FIG. 4F.

Figure 5A:
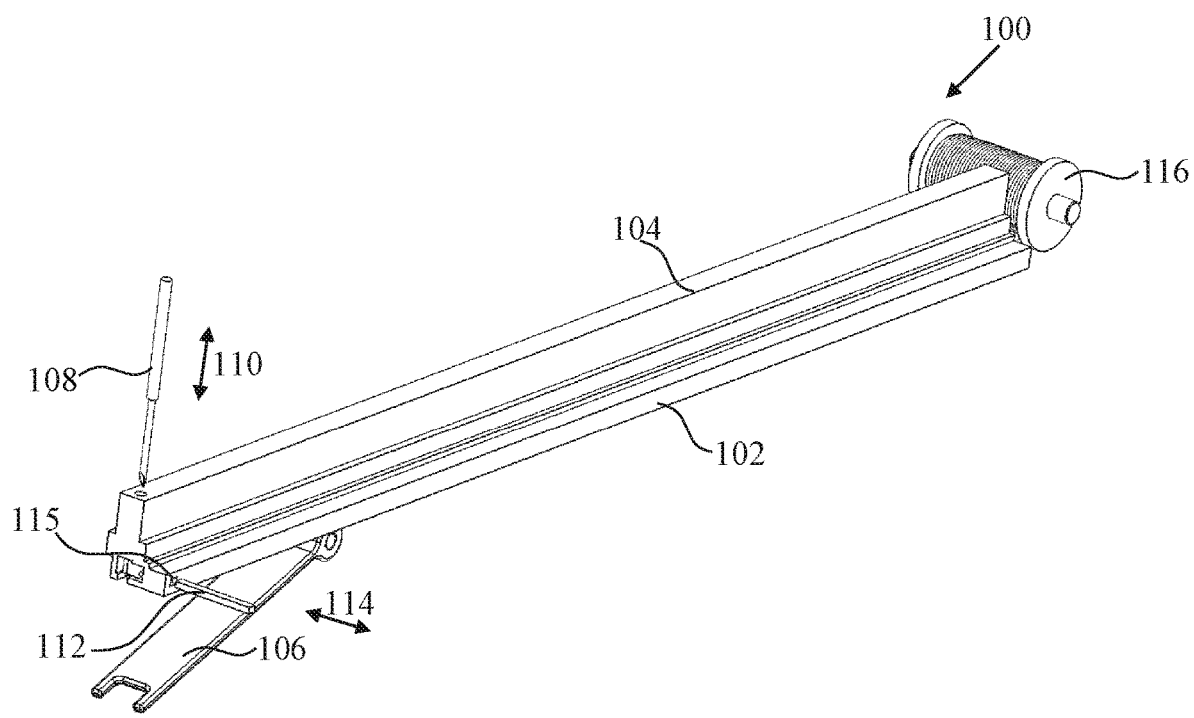
FIG. 5A shows a partial view of a suturing device according to an embodiment of this disclosure, with external casing, lever and other elements of its mechanism removed for ease of illustration.

Referring now to FIG. 5A, showing a part of the device generally designated 100. In accordance with another embodiment of this disclosure, the device has a holder 102 with cover 104 holding a series of anchoring units, as described below. Device 100 also includes a tissue guide 106, displacing member 108 that can reciprocate in a forward-rearward direction, as represented by arrow 110 ("forward" being the downward direction in FIG. 5A), as will be illustrated further below, displacing member 108 configured for displacing tissue-penetrating portion of the anchoring units into the tissue. The device also includes an auxiliary displacing member 112 that can reciprocate in a lateral direction, as represented by arrow 114, towards and away from the cassette. Also seen in FIG. 5A is a bobbin 116 with thread 118 extending therefrom as seen in FIG. 5B and coupled to the coupling elements of all the anchoring units (see below).

Figure 5B:
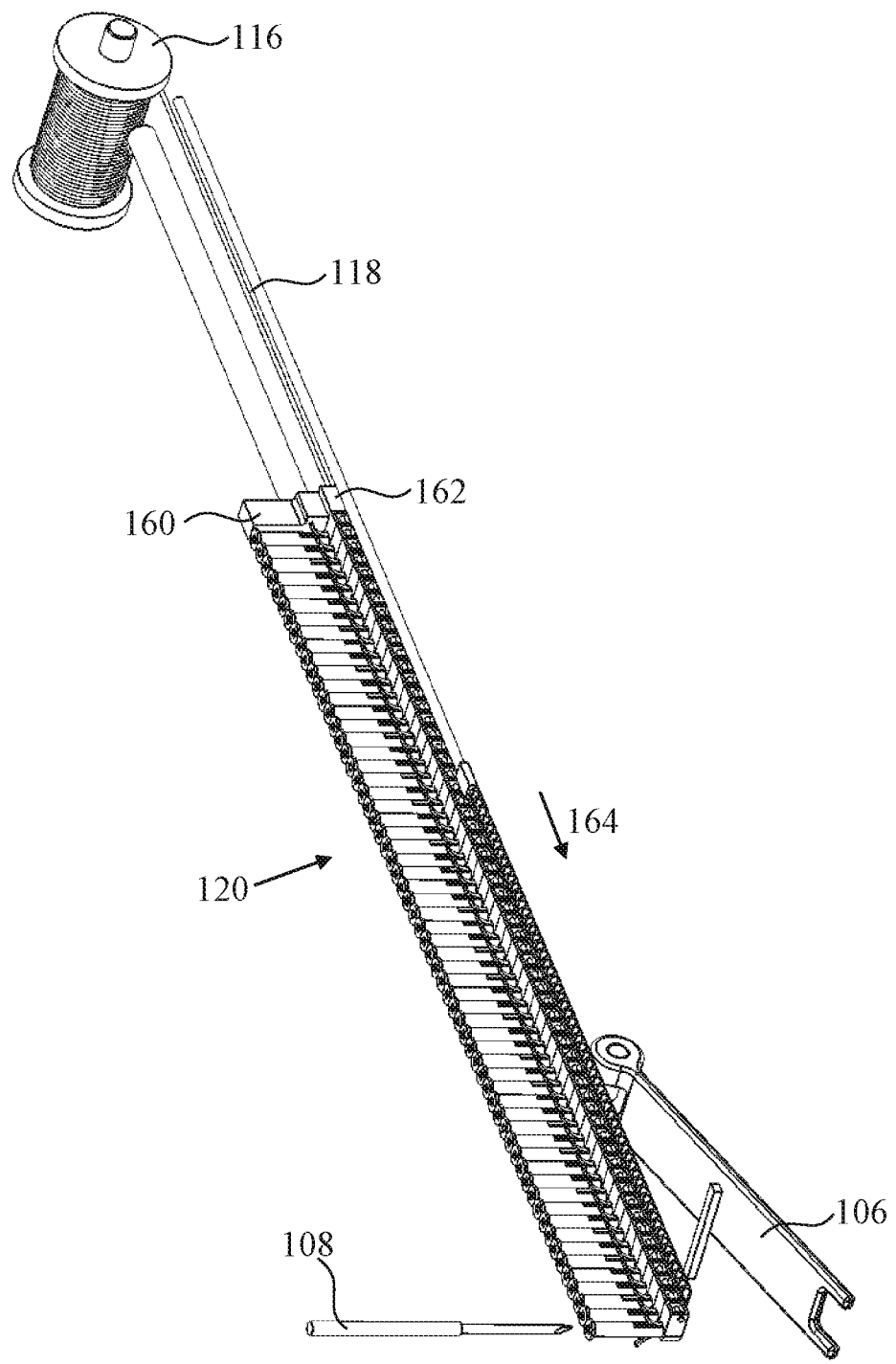
FIG. 5B shows a device of FIG. 5A after removal of the casing of the cassette to show the anchoring units.
Figure 5C:
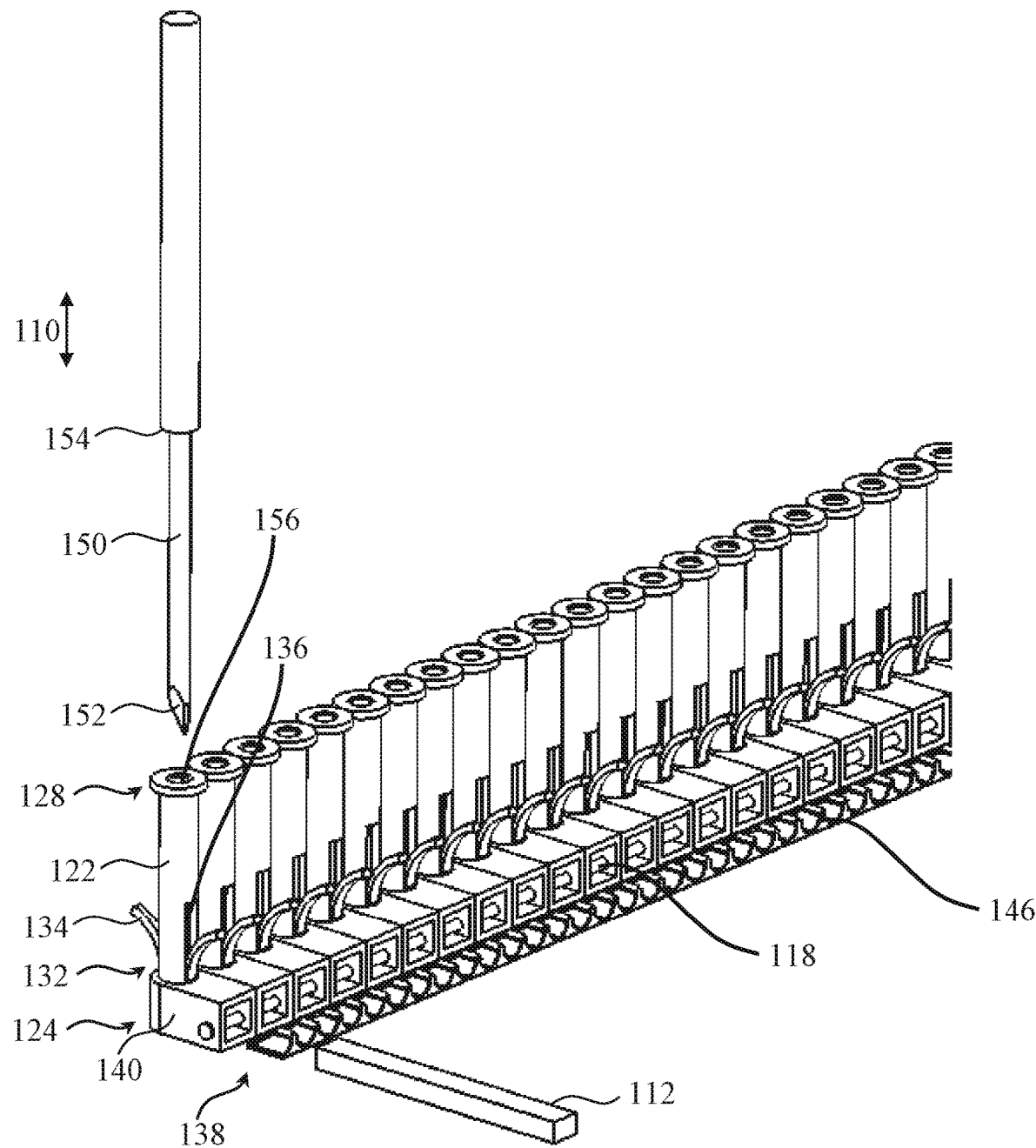
FIG. 5C is an enlarged view of the anchoring units and operative elements of the device shown in FIG. 5B.

As seen in FIGS. 5B and 5C, the device holds a plurality of anchoring units 120, each unit consisting of a tissue-penetrating shaft 122, extending between the first end portion 124 having a tapered end 126 (seen in FIGS. 5E-5G), and a second opposite end portion 128 with a broader end disk 130. Positioned at the first end portion are anchoring elements 132 constituted by two opposite flaps 134 that can switch between a deployment state, in which they are accommodated within corresponding grooves 136 (and hence are flush with the surface of shaft 122 first end portion), and a deployed state in which the flaps extend laterally, as seen, for example in FIGS. 5C and 5G. The flaps are biased into the deployed state and consequently, once the shaft has been penetrated through the tissue, these flaps open and arrest retraction of the shaft back to the tissue.

Each of units 120 also include a coupling element 138 which has a first portion 140 coupled to the thread and a second portion 142 with bore 144 accommodating shaft 122. This provides for a slidable connection between the coupling element and the shaft, consequently when axially pushed by displacing member 108, the shaft passes through the bore 144 and into the tissue. The relative sliding action is arrested by the shaft's opposite end 128 by means of disk portion 130.

Figure 5D:
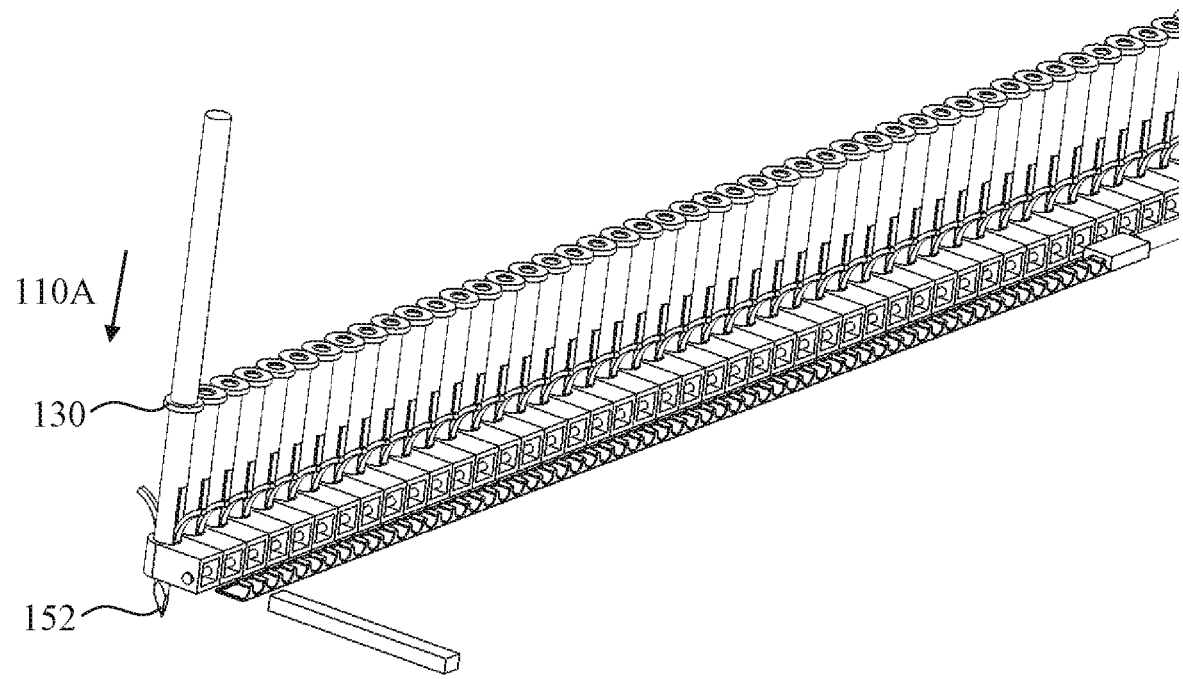
FIGS. 5D-5G are partial views of FIG. 5B in several operational steps.

Displacing member 108 has a forward narrow section 150 extending from a sharp tapered end 152 to shoulders 154. Shaft 122 is provided with a bore 156 dimensioned to receive the forward portion of 150 but not the section beyond shoulders 154. Consequently, once the forward section 150 is fully received within the bore (as can be seen in FIG. 5D), the tapered end thereof 152 forwardly extends from a front end of the bore (as seen in FIG. 5D). Once fully received, further forward axial displacement of displacing member 108 in the direction of arrow 110A will cause the entire shaft to slide downwards relative to the coupling element 142. In use, the entire device is pressed downwards against tissue guide 106 and consequently the front surface of the coupling element rests against (or is in close proximity with) the tissue's external surface. Thus, the relative forward axial sliding displacement of the displacing member will push the anchoring unit into the tissue with the passage being led by end 152.

Figure 5E:
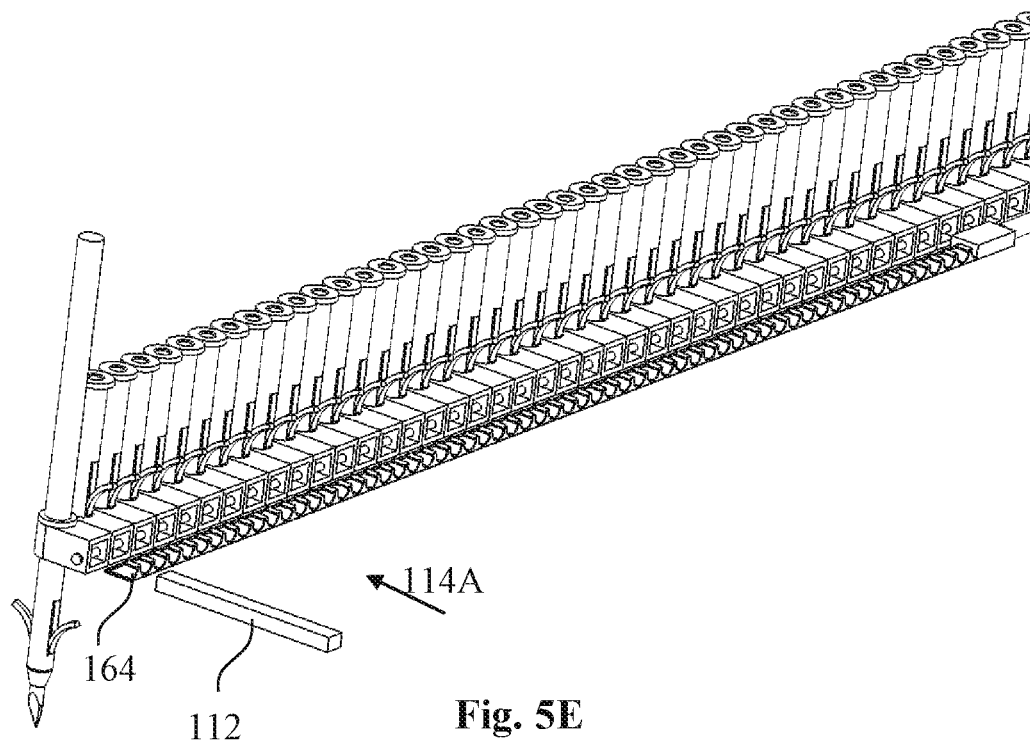
Figure 5F:
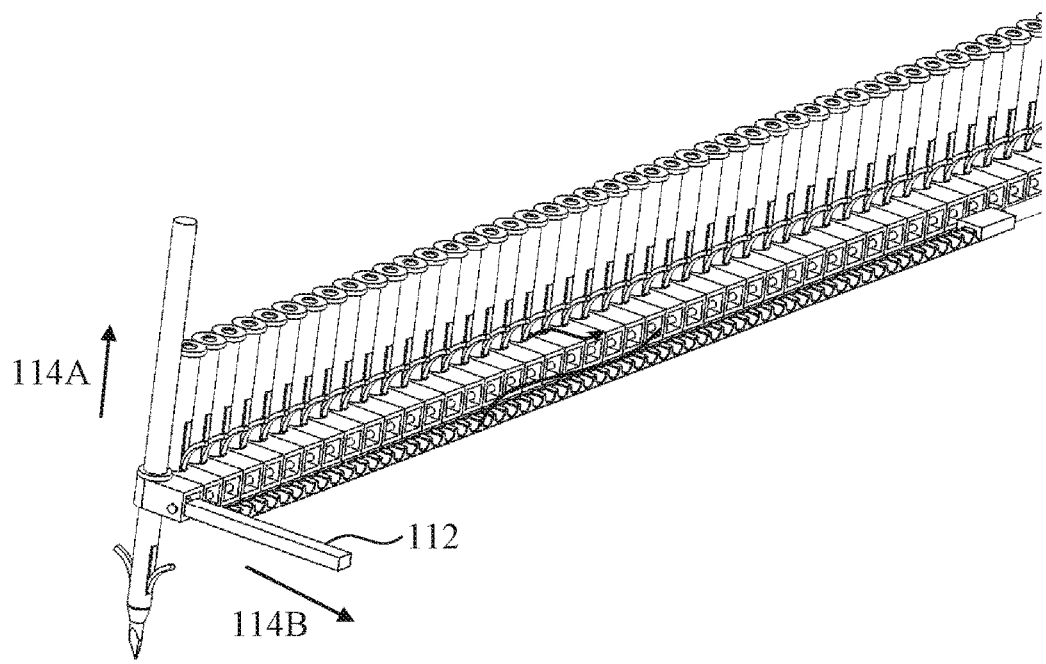
Figure 5G:
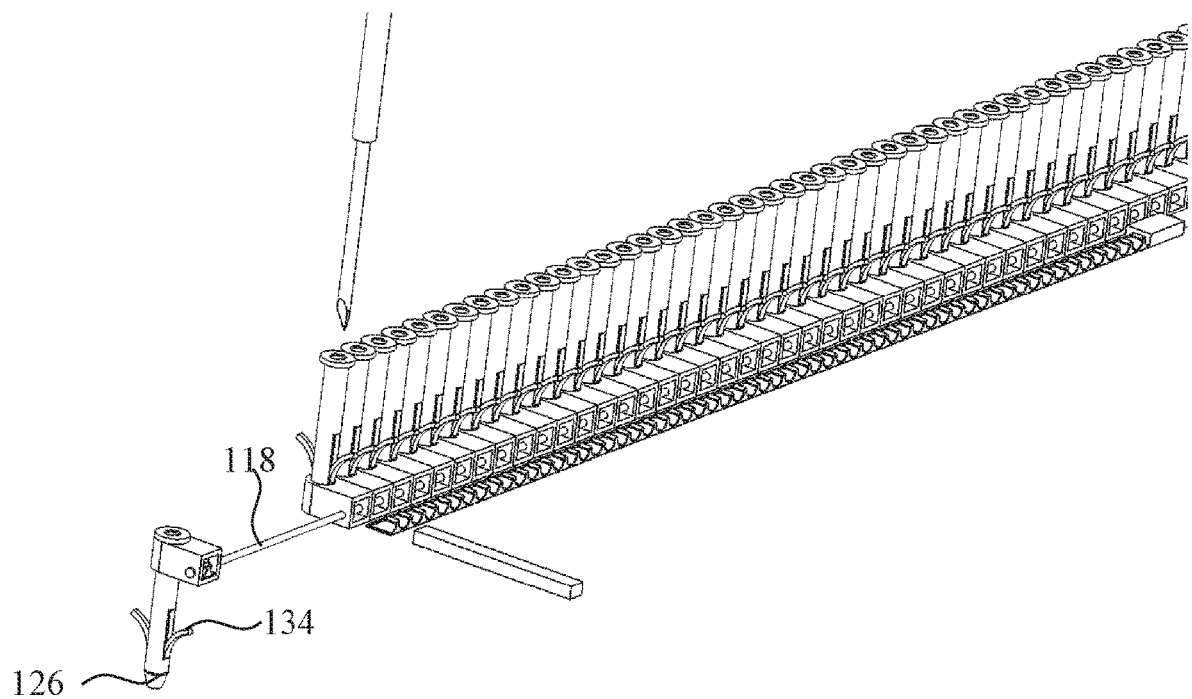

Once into the tissue, illustrated schematically in FIG. 5E, the flaps 134 open, arresting the shaft within the tissue and consequently axial retraction of displacing member 108 will not cause corresponding retraction of the shaft out of the tissue. The anchoring unit of this embodiment also comprises an auxiliary locking element 146 and a series of a plurality of such elements are held within the device, their number corresponding to that of the units. Once the anchoring unit is within the tissue (as shown in FIG. 5E), auxiliary displacing member 112 is moved laterally in the direction of the holder represented by arrow 114A (to pass through openings 115 defined in cover 104) and in this displacement laterally pushes the first-in-line of the auxiliary locking elements 146 into the open receiving end of coupling element 140, as seen in FIG. 5F. Through the engagement of the coupling element 140 and the auxiliary locking element 146, the thread 118 is locked within the coupling element, and subsequent pulling of the device away from the deployed anchoring unit, as seen in FIG. 5G, will release a certain length of thread from pulley 116. Then a subsequent anchoring unit may be deployed in the opposite tissue section, in the manner illustrated in FIGS. 4A-4F. It should be noted that prior to locking the coupling element of the subsequent anchoring unit once is deployed into the tissue, the section of the thread between the deployed units is tensioned to thereby bring the portions of the opposite sections into close proximity, again as illustrated in FIGS. 4A-4F.

Reference is again made to FIG. 5B, attention being drawn to main driving plunger 160 and auxiliary driving plunger 162 both of which are biased, e.g. by springs (not shown) in the direction represented by arrow 164. This provides a directional bias on the respective anchoring units and auxiliary locking elements so that after deployment of the first-in-line anchoring unit, a subsequent unit and auxiliary coupling element come into position to become the consecutive first-in-line unit.

Figure 6D:
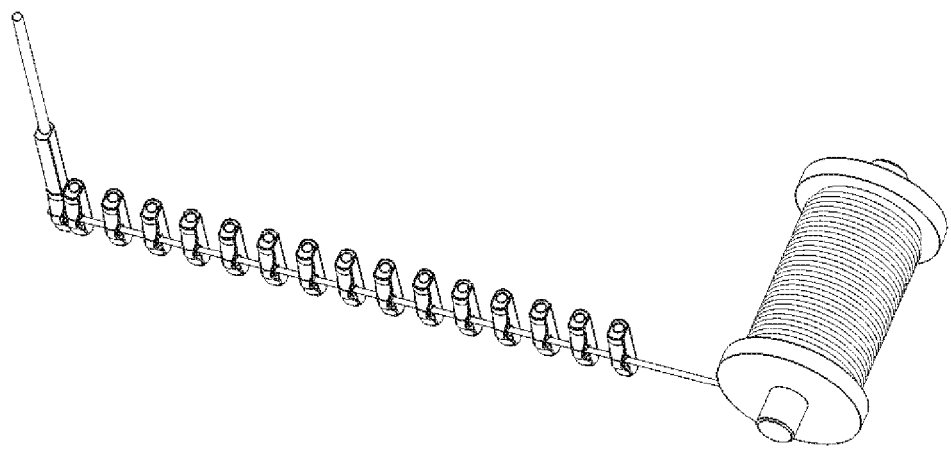
FIG. 6D shows the system of FIG. 6C with the coupling elements removed.

Reference is now made to FIGS. 6A-6F illustrating another embodiment of this disclosure. In this embodiment the anchoring element 201, shown in FIG. 6A, and the coupling element 240, shown in FIG. 6B are separate elements, linked to one another by the suturing thread, as will be explained below.

The anchoring element 201 is provided with an aperture 203, through which the thread passes (see also below); the anchoring element has a longitudinal bore 256 extending between the opposite anchoring ends—a rear end 228 and a front end 224, the front end being tapered. The anchoring element 201 is inserted into the tissue, in a manner similar to that shown in the embodiments of FIGS. 5A-5G, using a displacing member 208 (seen, for example, in FIG. 6C) with a front sharp tapered portion that is inserted into bore 256 with its front end protruding out of front end 224 and in this manner is inserted into the tissue.

Coupling element 240 has a generally prismatic shape arranged about a hollow space 241 with two lateral walls having bores 243. The thread 218 passes through the two opposite bores 243, and thus extends between the bores within space 241. The coupling element 240 also comprises an auxiliary locking element 246, formed with a ridge 247 extending from its slanted lead end 249, and a rear end 245. Once auxiliary locking element 246 is pushed into the hollow space 241, the thread 218 slides over the slanted portion 249 and then becomes locked in the coupling element, between the ridge 247 and the upper interior face 251 of coupling element 240, as illustrated in FIG. 6F.

Figure 6E:
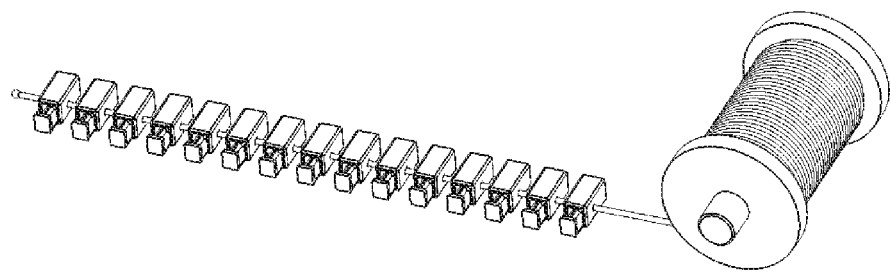
FIG. 6E shows the system of FIG. 6C with the anchoring elements removed.
Figure 6F:
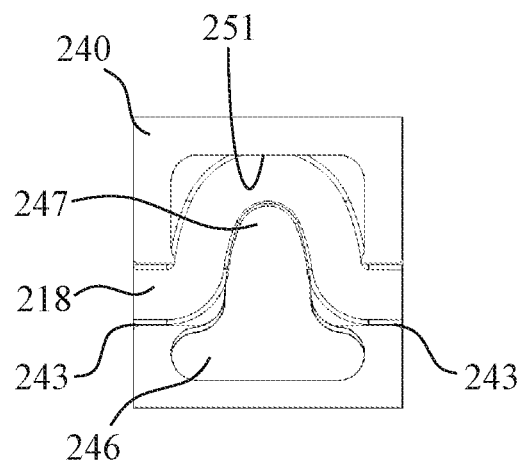
FIG. 6F is a schematic cross-section through the coupling element of FIG. 6B showing the manner of tight coupling with the thread.
Figure 6G:
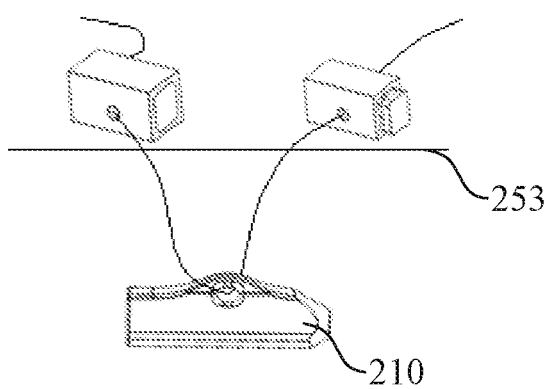
FIG. 6G is a schematic cross-section through a tissue with a deployed anchoring unit, according to the embodiments of FIGS. 6A-F.

The system 200 having an arrangement of the anchoring units and their elements, prior to their deployment, is shown in FIGS. 6C-6E. The thread 218 passes alternatingly through consecutive apertures 203 of the anchoring elements and bores 243 of the coupling elements 240. In other words, the anchoring elements and coupling elements are alternately fitted along the thread 218. The displacing member 208, similar to 108 in the embodiment shown for FIGS. 5A-5G, is activated through pushing the first-in-line of the anchoring elements 201 into the tissue. Once inserted, the coupling element 240 is pushed against the external tissue surface and then the auxiliary displacing member (not shown), similar to that of member 112 seen in FIG. 5C, pushes the rear end 245 of auxiliary locking member 246 into the locking position, shown in FIG. 6F. In this manner, an anchoring unit 201 with two independent elements, i.e. an anchoring element 201 within the tissue (represented schematically by line 253 in FIG. 6G) and a coupling element 240,246 outside the tissue which is locked to a thread, is formed, as seen in FIG. 6G.

During deployment, the thread 218 is continuously unwound from the bobbin 216. There is typically an associated mechanism which may provide a counter-force, in order to permit tensioning of the thread. The rotation of the bobbin 216 may be manually controlled to tightly tension the thread, after deployment of the unit, to bring the two opposite tissue sections close to one another. The tensioning mechanism may also be operable and controlled by mechanical means or electrical motors.

The invention claimed is:

1. A suturing device for suturing together two tissue sections, comprising:
   one or more suturing threads;
   a holder;
   a plurality of consecutive anchoring units disposed within the holder for deployment in a tissue section, the anchoring units being slidably disposed along the one or more suturing threads, each of the anchoring units comprising a tissue-anchoring element located at one end and a thread-coupling element located at an opposite end and slidably coupled to the one or more suturing threads, the tissue-anchoring element and the thread-coupling element in each anchoring unit being connected together, each of the tissue-anchoring elements being configured to be inserted and secured within the tissue by the tissue-anchoring element passing entirely through the tissue and being deployed outside one side of the tissue while the thread-coupling element is located outside an opposite side of the tissue; and
   an actuation arrangement configured for deploying each anchoring unit such that the tissue-anchoring element is fixed into the tissue, and for manipulating the thread to bring each deployed unit into proximity of each other,
   wherein the one or more suturing threads are slidably coupled to the thread-coupling elements and extend between the thread-coupling elements of consecutive anchoring units, such that manipulating the one or more suturing threads brings a deployed unit into proximity with a previous deployed unit anchored in an opposite section of the tissue, and
   wherein each of the thread-coupling elements is configured to permit sliding of the one or more suturing threads there through, and configured with a locking arrangement for locking each of the thread-coupling elements to the one or more suturing threads and maintaining a portion of the one or more suturing threads in a tensioned state, once brought together by the sliding into the proximity with each other.

2. The device of claim 1, wherein the actuation arrangement comprises a displacing member axially reciprocating in a forward-rearward direction and configured for displacement of the anchoring unit or tissue-penetrating portion thereof to position the tissue-anchoring element within the tissue.

3. The device of claim 2, wherein
   said displacing member has an elongated forward portion defined between a tapered, tissue-penetrating end and a shoulder,
   said displacing member being configured for insertion of said forward portion through said bore, to thereby axially displace said tissue-penetrating portion into the tissue with said tapered end providing a tissue-penetrating passage therefor.

4. The device of claim 1, wherein the anchoring unit comprises
   a tissue-penetrating shaft axially extending between a first, tapered end portion and a second, opposite end portion,
   an anchoring element at said first end portion configured as flaps switchable between a deployment state in which they are flush with the surface of the shaft's first end portion and a deployed state and biased into the latter state in which they extend in the radial direction away from said surface to thereby arrest retraction of the shaft back through the tissue, and
   a coupling element associated with the shaft in an axially slidable manner.

5. The device of claim 4, wherein the actuation arrangement is configured to axially displace said shaft into the tissue, and/or wherein during displacement the shaft axially slides within an a bore defined by the coupling element whereby after deployment the coupling element is positioned at said second end portion.

6. The device of claim 1, comprising an auxiliary locking member fitting into said thread-coupling element to lock the thread in its tensioned state.

7. The device of claim 1, wherein the thread-coupling element is in rigid association with the tissue-anchoring element of the same unit to define together the anchoring unit.

8. The device of claim 1, wherein the tissue-anchoring element and the thread-coupling element of a unit are linked to one another by the one or more suturing threads.

9. The device of claim 8, wherein the one or more threads are slidably coupled to the tissue-anchoring element.

10. The device of claim 1, wherein said one or more threads pass through the thread-coupling elements of all tissue-anchoring members.

11. A cassette for a suturing device of claim 1.

12. The cassette of claim 11, wherein each of the anchoring units has a tissue-penetration portion with an axial bore.

13. The cassette of claim 11, wherein each anchoring unit defines a tissue penetration axis between a first, tapered, end portion forwardly directed and a second, opposite end portion; the anchoring unit being fitted at said first end portion and the coupling element being at the opposite, second end portion.

14. The cassette of claim 11, wherein each anchoring unit has
   a tissue-penetrating shaft axially extending between a first, tapered end portion and a second, opposite end portion,
   an anchoring element at said first end portion configured as flaps switchable between a deployment state in which they are flush with the surface shaft's first end portion and a deployed state and biased into the latter state in which they extend in the radial direction away from said surface to thereby arrest retraction of the shaft back through the tissue, and
   a coupling element associated with the shaft in an axially slidable manner.

15. The cassette of claim 11, comprising a series of consecutive auxiliary locking members corresponding to the anchoring units for fitting into the thread-coupling elements to lock the thread in its tensioned state.

16. The cassette of claim 11, wherein the thread-coupling element is in rigid association with the anchoring element of the same unit to define together the anchoring unit.

17. The cassette of claim 11, wherein the one or more threads are slidably coupled to the tissue-anchoring element, or wherein said one or more threads pass through the coupling elements of all anchoring members.

18. The cassette of claim 11, wherein the anchoring units are dimensioned for penetrating through fascia with the tissue-anchoring element being deployed at the fascia's interior.

19. The cassette of claim 11, wherein the thread-coupling element is coupled to the one or more threads in a manner permitting one-directional movement of the thread relative to said thread-coupling element.

20. A tissue suturing system for suturing together two tissue sections, the tissue suturing system comprising:
one or more suturing threads;
an arrangement of a plurality of consecutive anchoring units for deployment in a tissue, the anchoring units being slidably disposed along the one or more suturing threads, each of the anchoring units comprising a tissue-anchoring element located at one end and a thread-coupling element located at an opposite end and slidably coupled to the one or more suturing threads, the tissue-anchoring element and the thread-coupling element in each unit being connected together;
each tissue-anchoring element being configured to be inserted and secured within the tissue by the tissue-anchoring element passing entirely through the tissue and being deployed outside one side of the tissue while the thread-coupling element is located outside an opposite side of the tissue; and
an actuation arrangement configured for deploying each anchoring unit such that the tissue-anchoring element is fixed into the tissue, and for manipulating the thread to bring each deployed unit into proximity of each other,
wherein the one or more suturing threads are slidably coupled to the thread-coupling element and extending between thread-coupling elements of consecutive anchoring units, such that manipulating the one or more suturing threads brings a deployed unit into proximity with a previous deployed unit, and
wherein each of the thread-coupling elements is configured to permit sliding of the one or more suturing threads therein, and configured with a locking arrangement for locking each of the thread-coupling elements to the one or more suturing threads and maintaining a portion of the one or more suturing threads in a tensioned state, once brought together by the sliding into the proximity with each other.

21. The device of claim 1, wherein the thread-coupling elements and the one or more suturing threads are configured so that the one or more suturing threads are controllably coupled with the thread-coupling elements.

22. The device of claim 1, wherein each thread-coupling element is configured to allow only for unidirectional sliding of the one or more suturing threads vis-a-vis the thread-coupling elements.

23. The device of claim 22, wherein each thread-coupling elements is formed with an inner cavity extending along a bore and having a jagged cross-sectional profile.

24. The device of claim 22, wherein each thread-coupling element is formed with an inner cavity extending along a bore having a jagged cross-sectional profile formed by wedge-shaped teeth extending inwardly into the bore, and the one or more suturing threads passing through the bore of each thread-coupling element is structured with a plurality of complementary wedge-like teeth extending radially from an outer surface of the one or more suturing threads, and wherein the complementary teeth are configured in a manner permitting engagement with the teeth of the bore of each thread-coupling element such that only a unidirectional movement of the one or more suturing threads is enabled through the bore of each thread-coupling element.

\* \* \* \* \*